US007856138B2

(12) United States Patent
Nehmadi et al.

(10) Patent No.: US 7,856,138 B2
(45) Date of Patent: Dec. 21, 2010

(54) SYSTEM, METHOD AND COMPUTER SOFTWARE PRODUCT FOR INSPECTING CHARGED PARTICLE RESPONSIVE RESIST

(75) Inventors: Youval Nehmadi, Modiin (IL); Ovadya Menadeva, Modiin (IL); Sergey Latinsky, Modiin (IL); Zamir Abraham, Rehovot (IL); Orit Afek, Ness-Ziona (IL)

(73) Assignee: Applied Materials Israel, Ltd., Rehovot (IL)

( * ) Notice: Subject to any disclaimer, the term of this patent is extended or adjusted under 35 U.S.C. 154(b) by 1291 days.

(21) Appl. No.: 11/361,104

(22) Filed: Feb. 23, 2006

(65) Prior Publication Data

US 2006/0266833 A1  Nov. 30, 2006

Related U.S. Application Data

(60) Provisional application No. 60/656,620, filed on Feb. 24, 2005.

(51) Int. Cl.
*G06K 9/00* (2006.01)
(52) U.S. Cl. ...................................... 382/144; 382/145
(58) Field of Classification Search .......... 382/141–153
See application file for complete search history.

(56) References Cited

U.S. PATENT DOCUMENTS

| | | | | |
|---|---|---|---|---|
| 4,863,548 A * | 9/1989 | Lee | ........................ | 156/345.24 |
| 5,182,718 A * | 1/1993 | Harafuji et al. | ................ | 430/30 |
| 5,343,292 A * | 8/1994 | Brueck et al. | ................ | 356/509 |
| 5,447,810 A * | 9/1995 | Chen et al. | ...................... | 430/5 |
| 5,572,598 A * | 11/1996 | Wihl et al. | ................... | 382/144 |
| 5,847,818 A * | 12/1998 | Lin et al. | .................. | 356/124.5 |
| 6,323,938 B1 * | 11/2001 | Grodnensky et al. | .......... | 355/77 |
| 6,368,879 B1 * | 4/2002 | Toprac | .......................... | 438/5 |
| 6,388,253 B1 * | 5/2002 | Su | ............... | 250/310 |
| 6,440,759 B1 * | 8/2002 | Commons et al. | ............... | 438/7 |
| 6,868,175 B1 * | 3/2005 | Yamamoto et al. | .......... | 382/145 |
| 7,014,955 B2 * | 3/2006 | Chang et al. | .................... | 430/5 |
| 7,149,998 B2 * | 12/2006 | Li | ............... | 716/19 |
| 7,155,698 B1 * | 12/2006 | Gennari | ....................... | 716/19 |
| 7,298,496 B2 * | 11/2007 | Hill | .............. | 356/512 |
| 7,422,828 B1 * | 9/2008 | Kim | .............................. | 430/5 |
| 2003/0044692 A1 * | 3/2003 | Liu et al. | ....................... | 430/5 |
| 2003/0044696 A1 * | 3/2003 | Liu et al. | ....................... | 430/5 |
| 2003/0208728 A1 * | 11/2003 | Pierrat | ........................... | 716/4 |
| 2004/0081350 A1 * | 4/2004 | Kitamura et al. | ............ | 382/149 |
| 2004/0126672 A1 * | 7/2004 | Li | ............... | 430/5 |
| 2004/0190007 A1 * | 9/2004 | Barber et al. | ................ | 356/625 |
| 2005/0164096 A1 * | 7/2005 | Hong et al. | ..................... | 430/5 |
| 2005/0226494 A1 * | 10/2005 | Yamamoto et al. | .......... | 382/149 |
| 2006/0000964 A1 * | 1/2006 | Ye et al. | ................... | 250/208.1 |

(Continued)

*Primary Examiner*—Manav Seth
(74) *Attorney, Agent, or Firm*—SNR Denton US LLP

(57) ABSTRACT

A system software product and a method for evaluating a mask, the method including the stages of: defining multiple CD measurement target windows; defining multiple pattern recognition windows such that the multiple CD measurements windows do not overlap the multiple pattern recognition windows, wherein each CD measurement target window and an associated pattern recognition window are positioned within a measurement area that is scannable without introducing a substantial mechanical movement; performing multiple critical dimension measurements of multiple patterns of an object being manufactured by exposing the mask to radiation, wherein the performing comprises using at least one CD measurement target window and at least one pattern recognition window; and evaluating the mask.

20 Claims, 5 Drawing Sheets

U.S. PATENT DOCUMENTS

| | | | |
|---|---|---|---|
| 2006/0277520 A1* | 12/2006 | Gennari | 716/21 |
| 2007/0099091 A1* | 5/2007 | Tsai | 430/5 |
| 2007/0099098 A1* | 5/2007 | Tsai | 430/22 |
| 2008/0118850 A1* | 5/2008 | Takeuchi | 430/5 |
| 2009/0035667 A1* | 2/2009 | Ozawa | 430/5 |

* cited by examiner

SYSTEM, METHOD AND COMPUTER SOFTWARE PRODUCT FOR INSPECTING CHARGED PARTICLE RESPONSIVE RESIST

RELATED APPLICATION

This application is a nonprovisional of and claims priority to U.S. provisional application Ser. No. 60/656,620, filed 24 Feb. 2005, incorporated herein by reference.

FIELD OF THE INVENTION

This invention relates to systems, methods and computer software products for inspecting semiconductors wafers during circuit fabrication and, in particular, for inspecting resistive materials that respond to charged particle beams.

BACKGROUND OF THE INVENTION

Integrated circuits are very complex devices that include multiple layers. Each layer may include conductive material, isolating material while other layers may include semi-conductive materials. These various materials are arranged in patterns, usually in accordance with the expected functionality of the integrated circuit. The patterns also reflect the manufacturing process of the integrated circuits.

Integrated circuits are manufactured by complex multi-staged manufacturing processes. During this multi-staged process resistive material is (i) deposited on a substrate/layer, (ii) exposed by a photolithographic process, and (iii) developed to produce a pattern which defines some areas to be later etched.

Resistive materials are usually selected such as to be responsive to a light at a predefined narrow range of frequencies (wavelengths). A commonly utilized resistive material is responsive to 193 nm light emitted from ArF light sources. This resistive material is referred to as 193 nm resist.

Various inspection and failure analysis techniques have evolved for inspecting integrated circuits both during the fabrication stages, between consecutive manufacturing stages, either in combination with the manufacturing process (also termed "in line" inspection techniques) or not (also termed "off line" inspection techniques). Various optical as well as charged particle beam inspection tools and review tools are known in the art, such as the VeraSEM™, Compluss™ and SEMVision™ of Applied Materials Inc. of Santa Clara, Calif..

Manufacturing failures may affect the electrical characteristics of the integrated circuits. Some of these failures result from unwanted deviations from the required dimensions of the patterns. A "critical dimension" is the width of a patterned line or the distance between two patterned lines.

One of the goals of the inspection process is to determine whether the inspected wafer includes deviations from these critical dimensions. This inspection is usually done by charged particle beam imaging that provides the high resolution required to measure said deviations.

Various resistive materials are also responsive to charged particle beams, such as electrical beams emitted during a Scanning Electron Microscope (SEM) imaging. The 193 nm resist shrinks as a result of an interaction with the electron beam. The shrinkage is due to both quantum effects (breaking of chemical bonds) and localized heating effects. Thus, SEM imaging causes an unwanted change in the pattern imprinted upon a semiconductor.

Modern masks (also referred to as reticles) are used to generate integrated circuit patterns. Due to the very small dimensions of integrated circuit features the optical proximity correction (OPC) technique was developed. OPC involves adding various features to the mask such as to cause the required pattern to be printed. The two most common applications for OPC are linewidth differences between features in regions of different density (e.g., center vs. edge of an array, or nested vs. isolated lines), and line end shortening (e.g., gate overlap on field oxide). For the former case, scattering bars (sub-resolution lines placed adjacent to resolvable lines) or simple linewidth adjustments are applied to the design. For the latter case, "dogear" (serif or hammerhead) features are attached to the line end in the design.

In order to validate that the implementation of the OPC technique succeeded in providing the required pattern a large number of critical dimension measurements should be executed.

There is a need to perform OPC validation measurements without shrinking the measured resist.

SUMMARY OF THE INVENTION

A computer software product for evaluating a mask is provided. The product includes a computer-readable medium in which program instructions are stored, the instructions when executed by a computer cause the computer to define a critical dimension measurement sequence of multiple targets of an object produced by exposing the mask to radiation; wherein the definition comprises defining multiple CD measurement target windows, and to define multiple pattern recognition windows such that the multiple CD measurements windows do not overlap the multiple pattern recognition windows; wherein each CD measurement target window and an associated pattern recognition window are positioned within a measurement area that is scannable without introducing a substantial mechanical movement.

Conveniently, the program instructions, when executed by a computer further cause the computer to evaluate the mask in response to multiple measurements obtained during the critical dimension measurement window.

A system is provided. The system includes a charged particle scanner, adapted to scan multiple CD measurement target windows and multiple pattern recognition windows in order to measure multiple critical dimensions of multiple patterns of an object being manufactured by exposing a mask to radiation; and a computer, adapted to evaluate the mask in response to the measured multiple critical dimensions.

The invention provides a method for evaluating a mask, the method includes the stages of: defining multiple CD measurement target windows; defining multiple pattern recognition windows such that the multiple CD measurements windows do not overlap the multiple pattern recognition windows; wherein each CD measurement target window and an associated pattern recognition window are positioned within a measurement area that is scannable without introducing a substantial mechanical movement; performing multiple critical dimension measurements of multiple patterns of an object being manufactured by exposing the mask to radiation; wherein the performing comprises using at least one CD measurement target window and at least one pattern recognition window; and evaluating the mask.

Conveniently, one pattern recognition window does not overlap a second pattern recognition window.

Conveniently, the distance between each CD measurement target window and associated pattern recognition window is responsive to a positioning inaccuracy of the charged particle beam.

Conveniently, the location of the multiple pattern recognition windows is responsive to locations of the multiple CD measurement targets and to a pattern recognition window relevance zone.

Conveniently, each pattern recognition window includes a pattern recognition sub-window.

Conveniently, the number of pattern recognition windows is minimized.

Conveniently, multiple auto-focus windows are defined. These auto-focus windows do not overlap the multiple CD measurement target windows, and performing auto-focus sessions within at least one auto-focus window.

Conveniently, the multiple pattern recognition windows and the multiple auto-focus windows do not overlap.

Conveniently, the defining of multiple auto-focus windows is responsive to locations of the multiple CD measurement targets and to auto-focus window relevance zone.

Conveniently, the stage of defining multiple auto-focus windows comprises minimizing the number of auto-focus windows.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE DRAWINGS

The following description relates to charged particle microscopes, such as Scanning Electron Microscopes (SEMs), such as step and repeat type SEMs, in which a wafer is scanned by repetitive steps of scanning an area of the wafer (said area defined by the field of view of the SEM) and mechanically introducing a movement between the wafer and SEM to facilitate the scanning of another area. Said movement may also be implemented by electrostatic and/or magnetic fields introduced by various electrostatic and/or magnetic elements such as lens, deflectors and the like. It is noted that other charged particles and even photons may be utilized for detecting voltage contrast. It is further noted that this invention may also be implemented by introducing a substantially constant movement between the SEM and the wafer. The movement may be linear or even rotational, and/or any combination of both movements.

Figure 1:
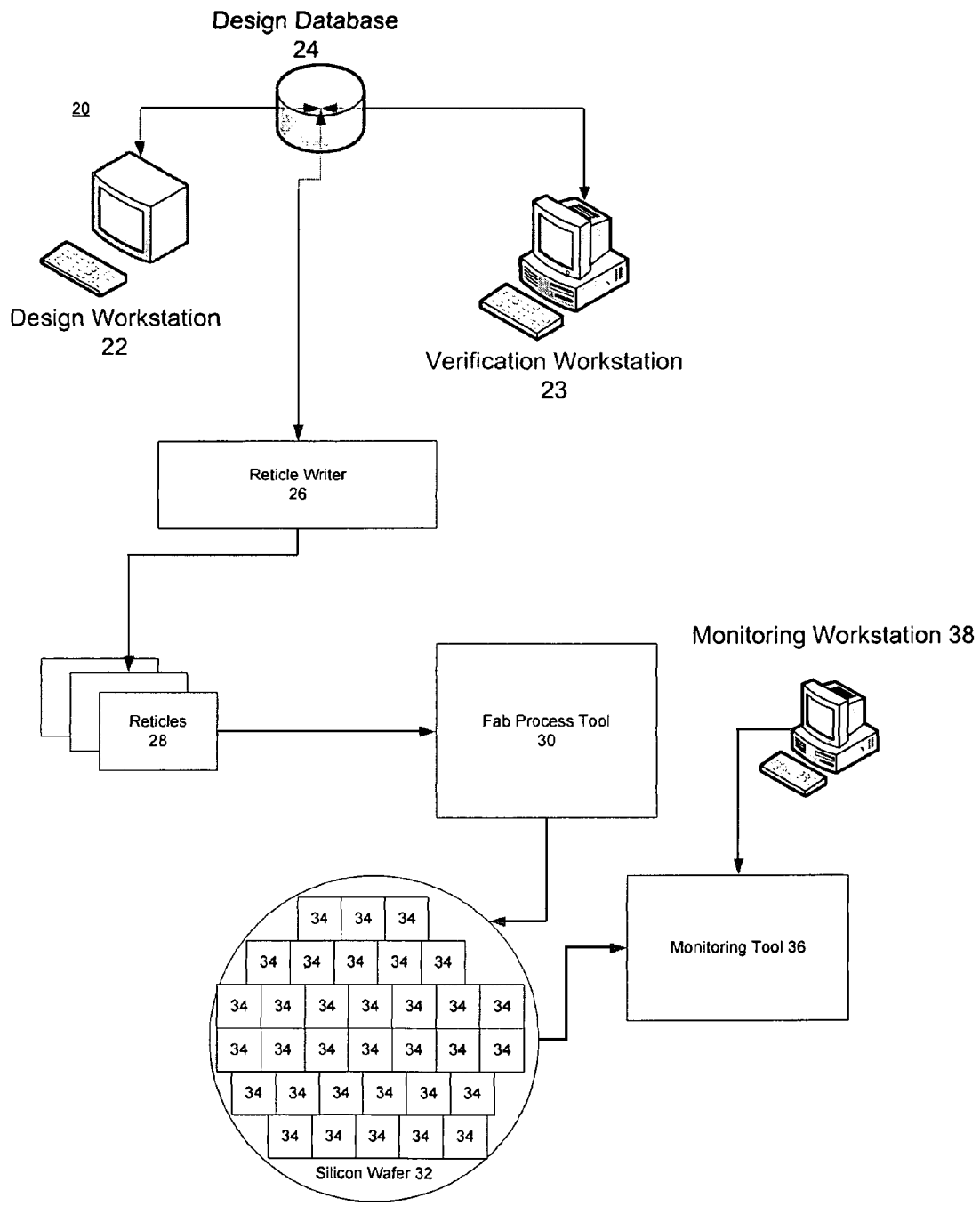
FIG. 1 is a schematic illustration of a system according to an embodiment of the invention.

FIG. 1 is a schematic, pictorial illustration of a system 20 for evaluating a mask, in accordance with an embodiment of the present invention. A design engineer, using EDA tools on a design workstation 22, designs elements of an integrated circuit (IC), from the logic synthesis down to the specific layout of circuit components. The design is stored in electronic form in a design database 24. The database specifies the set of masks that are to be used in producing the IC. The masks can be generated by applying OPC techniques. Optionally, workstation 22 generates, as a by-product of the IC design, a product diagnostic profile (PDP), which is also held in the design database. The PDP is typically generated interactively by the design engineer on workstation 22. Alternatively or additionally, elements of the PDP may be generated by the workstation automatically. Further alternatively or additionally, a separate computer (not shown) may be used to generate all or part of the PDP based on the information in database 24. The PDP may include a definition of CD measurement targets that can be used for evaluating the mask, and especially for determining if the applied OPC technique achieved its goal-printing required pattern on the IC.

A verification engineer checks the design in database 24 using a verification workstation 23. Such verification typically includes, for example, design rule checking, as well as other means known in the art for physical and functional design verification. Workstation 23 may also add data to the PDP, automatically or through interaction with the verification engineer.

Table I below shows a typical EDA workflow, from initial circuit specification through to tape-out. The flow steps are shown here by way of example, as background for creation of the PDP, which is described below. Those skilled in the art will recognize that there may be many variations and additions to the sequence of steps listed below, and that accordingly there may be variations, as well, in the methods used to derive the PDP data from different EDA tools.

TABLE I

| Step | Function |
| --- | --- |
| Behavioral modeling | Check functional aspects of design |
| Simulation | Check for design accuracy and faults |
| Logic synthesis | Create net list |
| Timing analysis | Check critical path and speed requirements |
| Place and route | Automated circuit layout |
| Layout | Manual changes to the circuit layout |
| RC extraction | Check parasitic capacitance and resistance in the circuit |
| Layout vs. schematic | Compare layout to net list design |
| Design rule check | Verify compliance with design rules |
| Stream GDS2 | Store design data in a geometrical polygon-based architecture |
| OPC | Optical proximity corrections - to accommodate optical artifacts in photolithography |
| Tape-out | Complete mask design |

When the design is complete, it is transferred to the fab for production. A reticle writer 26 generates a set of reticles 28 based on the design in database 24. The reticles are then used in a set of fab process tools, represented in the figure by a tool 30, to produce IC dies 34 on a silicon wafer 32. Of course, this view is grossly oversimplified, and multiple different process steps are typically applied to each layer on the wafer. In other words, each reticle 28 maps to a sequence of several process steps in the fab.

After each process step, wafer 32 may be inspected or otherwise tested by a monitoring tool 36. Typically, various different monitoring tools are used at different steps in the process. For example, a scanning electron microscope (SEM), such as the VeritySEM™, SEMVision™ or NanoSEM™ system, produced by Applied Materials (Santa Clara, Calif.), may be used for defect review and/or critical dimension measurements. As another example, an optical inspection system, such as the CompasS™ or ComPLUS™ system, also produced by Applied Materials, may be used for bright-field or dark-field defect inspection. Alternatively, other types of inspection tools may be used, as may electronic test instruments, as are known in the art. Some particular test applications are described below in greater detail.

The specific types of tests to be performed by monitoring tool 36, and the locations on dies 34 at which the tests are to be applied, are selected based on data from the PDP in design database 24. Typically, a process engineer uses a monitoring workstation 38 to select and set up the tests interactively, based on the PDP data. The test results may be reviewed on workstation 38. When a defect or other process deviation is observed by monitoring tool 36, the results are used in making adjustments to process tool 30 in order to correct and avoid defects in subsequent wafers. The results may also be used for proactive monitoring—to refine the test procedure so as to focus on sites and regions that are known to be susceptible to defects.

Workstations 22, 23 and 38 typically include general-purpose computers, running suitable software for designing masks, for applying OPC techniques and the like. Monitoring tool 36 typically includes a computer processor, as well, with suitable software for carrying out testing and inspection functions based on the PDP data in the design database. Alternatively or additionally, the monitoring can be based upon other databases.

Thus, software for the purposes of the present invention typically comprises an EDA program component, for use on workstations 22 and/or 23, and a process monitoring program component, for use on workstation 38 and/or monitoring tool 36. The software for the workstations and the monitoring tool may be provided in electronic, optical and/or magnetic form, over a network, for example, or it may alternatively be supplied on tangible media, such as CD-ROM.

Figure 2:
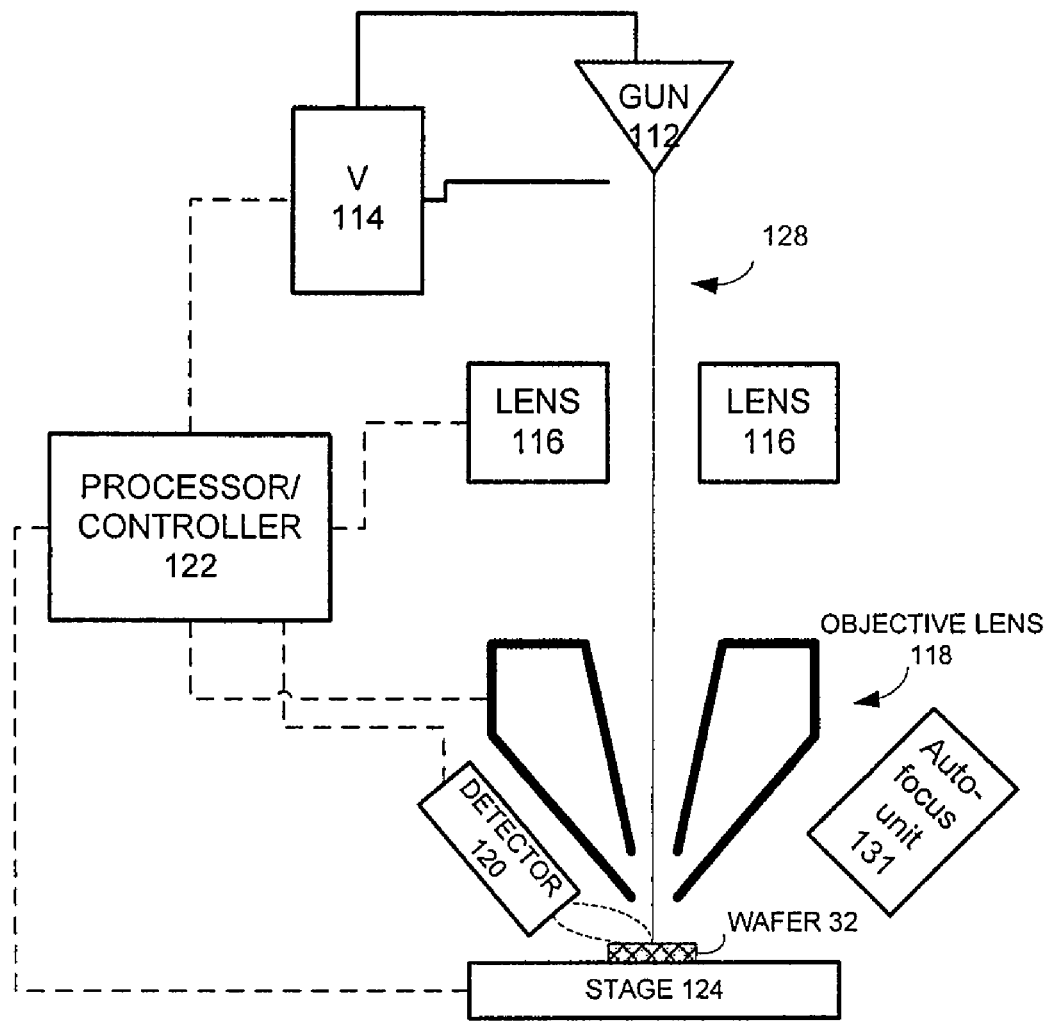
FIG. 2 is a schematic illustration of a portion of a scanning electron microscope, in accordance with an embodiment of the invention.

Referring to FIG. 2, a monitoring tool 36 such as SEM 36 is depicted, in accordance with an embodiment of the invention. SEM 36 includes electron gun 112, subjected to various voltages, such as an acceleration voltage that is schematically described as acceleration power source 114, first electron lens 116, magnetic-electrostatic objective lens 118, detector 120, controller/processor 122, stage 124 and auto-focus unit 131. Lenses 116 and 118 are controlled by controller/processor 122 to focus, direct and scan the charged particle beam. The lenses also may be operable to shape the charged particle beam in manners known in the art. Each of said components/units is well known in the art and thus do not require a detailed description. Briefly, SEM 36 is operable to generate a charged particle beam (especially by means of electron gun 112 and power source 114), to direct and focus the beam onto a specimen (such as wafer 32) and to scan the charged particle beam 128. Wafer 32 is placed on stage 124.

Electron gun 112, acceleration power source 114, first electron lens 116, magnetic-electrostatic objective lens 118, detector 120, stage 124 and controller/processor 122 form a scanner that is adapted to scan multiple CD measurement target windows and multiple pattern recognition windows in order to measure multiple critical dimensions of multiple patterns of an object being manufactured by exposing a mask to radiation.

Controller/processor 122 or workstation 38 can evaluate the mask in response to the measured multiple critical dimensions. The evaluation can include comparing the patterns of wafer 32 to expected patterns. The expected patterns can be stored in design database 24.

According to an embodiment of the invention SEM 36 is operated according to a measurement recipe. The measurement recipe can be generated and/or updated by a user of SEM 36, by one or more users of workstations 22, 23 and 36 and the like. The measurement recipe can be stored at SEM 36, at design database 24 or at any of workstations 22, 23 and 38.

The measurement recipe includes definitions of multiple pattern recognition windows, multiple CD measurement target windows and optionally multiple auto-focus windows. A CD measurement window does not overlap with other windows.

Conveniently, one pattern recognition window does not overlap a second pattern recognition window.

Conveniently, the distance between each CD measurement target window and associated pattern recognition window is responsive to a positioning inaccuracy of the charged particle beam.

Conveniently, the multiple pattern recognition window are located in response to locations of the multiple CD measurement targets and to a pattern recognition window relevance zone.

Figure 3:
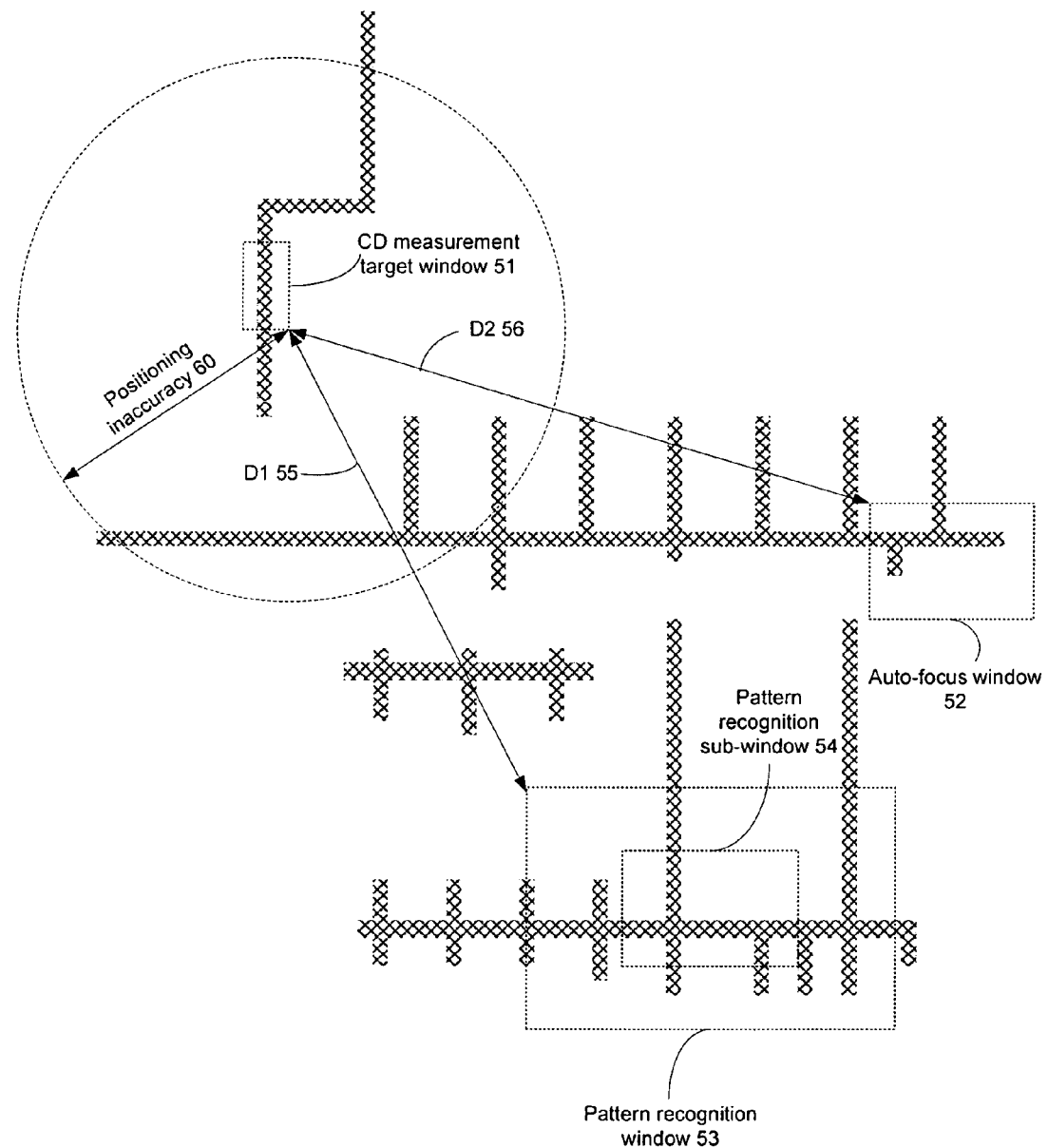
FIG. 3 is a schematic illustration of a portion of an inspected wafer, in accordance with an embodiment of the invention.

FIG. 3 illustrates a portion 33 of wafer 32 according to an embodiment of the invention. Portion 33 includes multiple patterns (illustrated by partially filled boxes), a CD measurement target window 51, an auto-focus window 52, a pattern recognition window 53 and a pattern recognition sub-window 54. The distance (Dl 55) between the CD measurement target window 51 and the pattern recognition window 53, and the distance (D2 56) between the CD measurement target window 51 and the auto-focus window 52 is bigger than the positioning inaccuracy (60) of SEM 36. It is noted that windows 51-53 can be scanned by SEM 36 without introducing a mechanical movement between wafer 32 and SEM 36.

Figure 4:
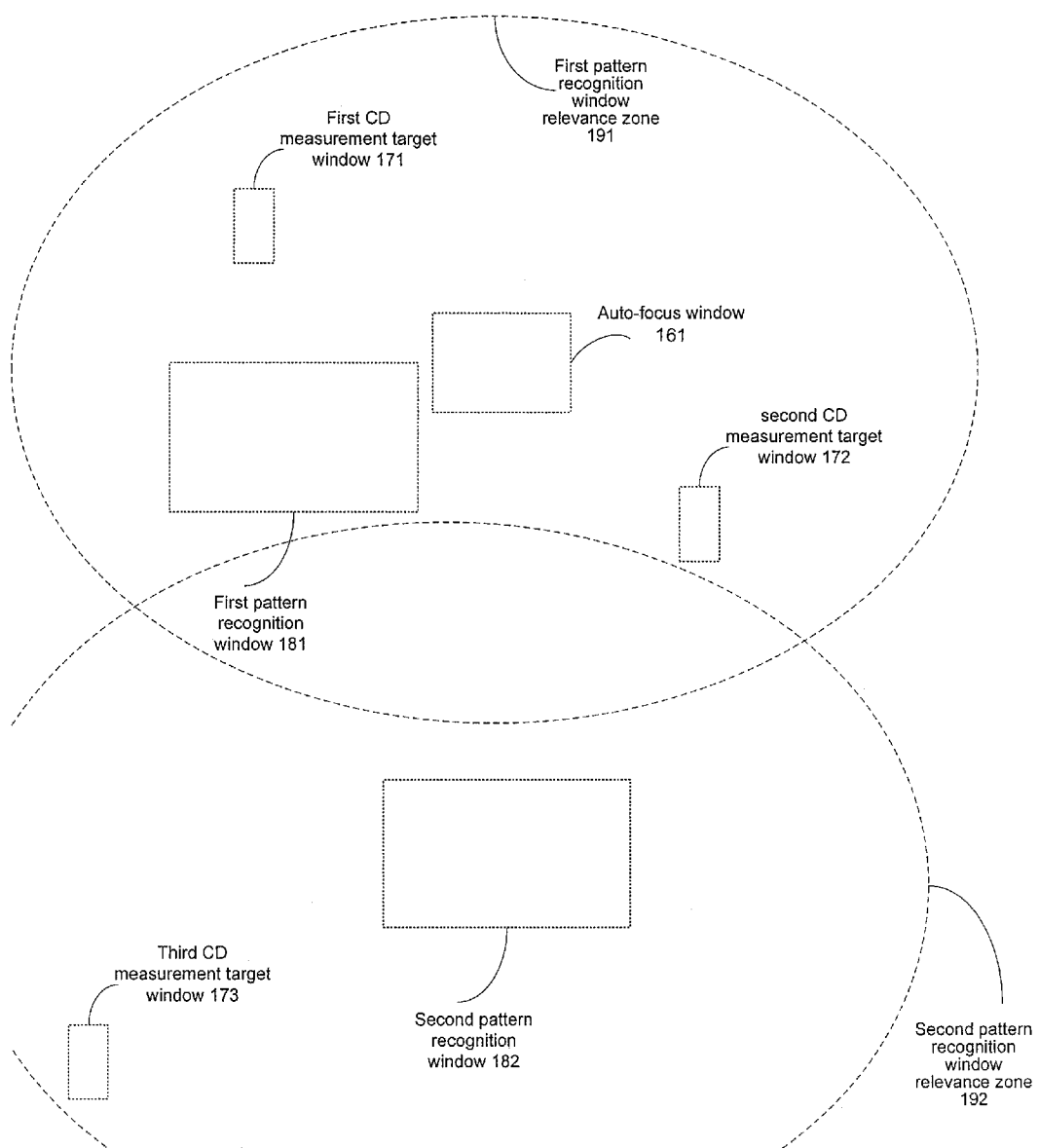
FIG. 4 is a schematic illustration of a portion of an inspected wafer, in accordance with an embodiment of the invention.

FIG. 4 illustrates a portion 37 of wafer 32 according to an embodiment of the invention.

Portion 37 includes three CD measurement target windows 171, 172 and 173, a single auto-focus window 161 and two pattern recognition windows 181 and 182. These windows do not overlap. In addition, the first pattern recognition window 181 can be used for accurately locating the CD measurement targets within windows 171 and 172, as both windows 171 and 172 are located within a first pattern recognition window relevance zone 191 associated with the first pattern recognition window 181.

The second pattern recognition window 182 can be used for accurately locating the CD measurement target within window 173, as window 173 is located within a second pattern recognition window relevance zone 192 associated with the second pattern recognition window 182.

It is noted that the focus is determined using a single auto-focus window 161. It is further noted that other relations can be defined between the various windows. For example, the number of auto-focus windows can be two or three and the number of pattern recognition windows can be one or three.

Figure 5:
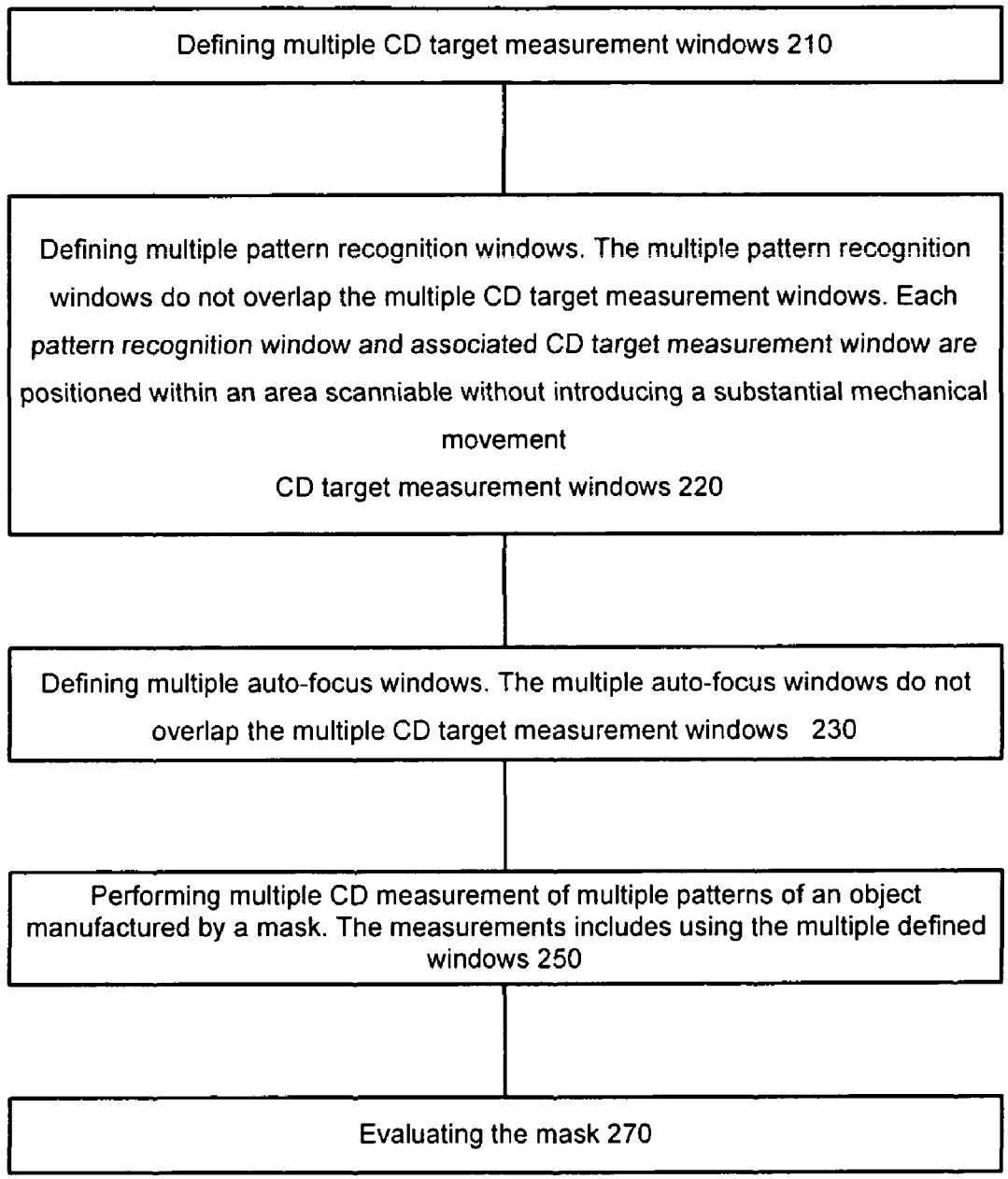
FIG. 5 is a flow chart illustrating a method for evaluating a mask according to an embodiment of the invention.

FIG. 5 illustrates method 200 for evaluating a mask, in accordance to an embodiment of the invention.

Method 200 starts by stage 210 of defining multiple CD measurement target windows.

Stage 210 is followed by stage 220 of defining multiple pattern recognition windows such that the multiple CD measurements windows do not overlap the multiple pattern recognition windows. Each CD measurement target window and an associated pattern recognition window are positioned within a measurement area that is scannable without introducing a substantial mechanical movement. Such a measurement area can be portion 33, first pattern recognition window relevance zone 191, second pattern recognition window relevance zone 192 and the like.

Conveniently, the defining of multiple pattern recognition windows is responsive to locations of the multiple CD measurement targets and to a pattern recognition window relevance zone. A pattern recognition window relevance zone represents a zone, surrounding the pattern recognition pattern, in which CD measurement targets can be accurately located based upon patterns that are recognized within the pattern recognition pattern.

Conveniently, each pattern recognition window includes a pattern recognition sub-window. The pattern recognition window can be regarded as including a field of view of the charged particle beam while the pattern recognition sub-window includes the patterns to be recognized.

Conveniently, stage 220 of defining multiple pattern recognition windows includes minimizing the amount of pattern recognition windows. Thus, if one pattern recognition window can be used for accurately locating a group of CD measurement targets then there is no need in defining different pattern recognition windows for each CD measurement target of the group.

Stage 220 is followed by stage 230 of defining multiple auto-focus windows that do not overlap the multiple CD measurement target windows. Conveniently, the multiple pattern recognition windows and the multiple auto-focus windows do not overlap. Conveniently, stage 230 of defining the multiple auto-focus windows is responsive to locations of the multiple CD measurement targets and to an auto-focus window relevance zone. Conveniently, the stage of defining multiple auto-focus windows includes minimizing the amount number of auto-focus windows.

Stage 230 is followed by stage 250 of performing multiple critical dimension measurements of multiple patterns of an object being manufactured by exposing the mask to radiation; wherein the performing includes using at least one CD measurement target window and at least one pattern recognition window.

A typical critical dimension measurement sequence of a single CD measurement target includes: receiving coordinates of the CD measurement target; introducing a mechanical movement (if necessary) between the wafer 32 and various components of SEM 36 (such as objective lens 18) such as to get to the vicinity of the CD measurement target; using a predefined auto-focus window for performing an auto-focus session; using a pattern recognition window for locating a pattern such as to accurately determine the position of the wafer in relation to various components of SEM 36; accurately locating the CD measurement target and measuring the critical dimension of the CD measurement target.

Stage 250 is followed by stage 270 of evaluating the mask.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

We claim:

1. A method for evaluating a mask, the method comprising: defining multiple Critical Dimension (CD) measurement target windows; defining multiple pattern recognition windows such that the multiple CD measurement target windows do not overlap the multiple pattern recognition windows, wherein each CD measurement target window and an associated pattern recognition window are positioned within a measurement area that is scannable without introducing a mechanical movement; performing multiple CD measurements of multiple patterns of an object being manufactured by exposing the mask to radiation, wherein the performing comprises using at least one CD measurement target window and at least one pattern recognition window; and evaluating the mask.

2. The method according to claim 1 wherein one pattern recognition window does not overlap a second pattern recognition window.

3. The method according to claim 1 wherein a distance between each CD measurement target window and associated pattern recognition window is responsive to a positioning inaccuracy of a charged particle beam.

4. The method according to claim 1 wherein the defining of multiple pattern recognition windows is responsive to locations of the multiple CD measurement target windows and to a pattern recognition window relevance zone.

5. The method according to claim 1 wherein each pattern recognition window includes a pattern recognition sub-window.

6. The method according to claim 1 wherein the stage of defining multiple pattern recognition windows comprises minimizing the number of pattern recognition windows.

7. The method according to claim 1 further comprising defining multiple auto-focus windows that do not overlap the multiple CD measurement target windows, and performing auto-focus sessions within at least one auto-focus window.

8. The method according to claim 7 wherein the multiple pattern recognition windows and the multiple auto-focus windows do not overlap.

9. The method according to claim 7 wherein the defining of multiple auto-focus windows is responsive to locations of the multiple CD measurement targets and to an auto-focus window relevance zone.

10. The method according to claim 7 wherein the stage of defining multiple auto-focus windows comprises minimizing the number of auto-focus windows.

11. A computer software product for evaluating a mask, the product comprising a tangible computer-readable medium in which program instructions are stored, the instructions when executed by a computer cause the computer to define a critical dimension (CD) measurement sequence of multiple targets of an object produced by exposing the mask to radiation, wherein the definition comprises defining multiple CD measurement target windows, and defining multiple pattern recognition windows such that the multiple CD measurement target windows do not overlap the multiple pattern recognition windows, wherein each CD measurement target window and an associated pattern recognition window are positioned within a measurement area that is scannable without introducing a mechanical movement.

12. The computer software product of claim 11 wherein the program instructions, when executed by the computer further cause the computer to evaluate the mask in response to multiple measurements obtained during a CD measurement window.

13. The computer software product of claim 11 wherein one pattern recognition window does not overlap a second pattern recognition window.

14. The computer software product of claim 11 wherein a distance between each CD measurement target window and the associated pattern recognition window is responsive to a positioning inaccuracy of a charged particle beam.

15. The computer software product of claim 11 wherein the definition further comprises defining multiple auto-focus windows that do not overlap the multiple CD measurement target windows.

16. The computer software product of claim 15 wherein the definition further comprises defining multiple pattern recognition windows and multiple auto-focus windows that do not overlap.

17. A system, comprising: a charged particle scanner, adapted to scan multiple Critical Dimension (CD) measurement target windows and multiple pattern recognition windows in order to measure multiple critical dimensions of multiple patterns of an object being manufactured by exposing a mask to radiation; and a computer, adapted to evaluate the mask in response to the measured multiple critical dimensions, wherein a distance between each CD measurement target window and an associated pattern recognition window is responsive to a positioning inaccuracy of a charged particle beam.

18. The system according to claim 17 wherein one pattern recognition window does not overlap a second pattern recognition window.

19. The system according to claim 17 wherein the multiple pattern recognition windows are located in response to locations of the multiple CD measurement targets and to a pattern recognition window relevance zone.

20. A system, comprising: a charged particle scanner, adapted to scan multiple Critical Dimension (CD) measurement target windows and multiple pattern recognition windows in order to measure multiple critical dimensions of multiple patterns of an object being manufactured by exposing a mask to radiation; a computer, adapted to evaluate the mask in response to the measured multiple critical dimensions; and an auto-focus unit, wherein the auto-focus unit defines a required focus parameter in response to detection signals from an auto-focus window scanned by the charged-particle scanner, and wherein the auto-focus window does not overlap with the multiple CD measurement target windows.

\* \* \* \* \*